(12) United States Patent
Vakharia et al.

(10) Patent No.: US 7,833,223 B2
(45) Date of Patent: Nov. 16, 2010

(54) TRI-BENDING SPHINCTERTOME

(75) Inventors: Omar Vakharia, Cincinnati, OH (US); Ifung Lu, Skokie, IL (US); Rudolph H. Nobis, Mason, OH (US); Christopher Paul Swain, London (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1223 days.

(21) Appl. No.: 11/381,006

(22) Filed: May 1, 2006

(65) Prior Publication Data

US 2008/0188879 A1  Aug. 7, 2008

(51) Int. Cl.
*A61B 18/14* (2006.01)
*A61B 17/32* (2006.01)

(52) U.S. Cl. .......................... 606/47; 606/113; 606/170
(58) Field of Classification Search ................ 606/47, 606/113, 170
See application file for complete search history.

(56) References Cited

U.S. PATENT DOCUMENTS

| | | | |
|---|---|---|---|
| 4,325,374 A * | 4/1982 | Komiya | 606/47 |
| 5,075,062 A | 12/1991 | Karpiel | |
| 5,810,807 A | 9/1998 | Ganz et al. | |
| 2003/0208219 A1 | 11/2003 | Aznoian et al. | |
| 2007/0255299 A1* | 11/2007 | Vakharia et al. | 606/170 |

FOREIGN PATENT DOCUMENTS

DE  3347122  * 6/1985  .................. 606/47

OTHER PUBLICATIONS

Hintze, et al., "Endoscopic Sphincterotomy Using an S-Shaped Sphincterotome in Patients with a Billroth II or Roux-en-Y Gastrojejunostomy", Endoscopy, 1997, 74-8, vol. 29(2).

* cited by examiner

*Primary Examiner*—Lee S Cohen
(74) *Attorney, Agent, or Firm*—Nutter McClennen & Fish LLP (57) ABSTRACT

Disclosed herein are devices and methods for forming multidirectional cuts in tissue. The tissue cutting devices disclosed herein generally include a flexible elongate member with at least first, second, and third wires that are at least partially constrained within or along a portion of the member. A distal portion of the wires is anchored on or within a portion of the elongate member. When tension is applied to at least one of the wires, such as by an actuator at a proximal end of the device, the elongate member bows while an unconstrained portion of the wire becomes exposed relative to the adjacent portion of the elongate member, assuming a tissue-cutting configuration.

21 Claims, 7 Drawing Sheets

TRI-BENDING SPHINCTERTOME

FIELD OF THE INVENTION

The present invention relates to surgical cutting devices, and in particular to multidirectional cutting devices.

BACKGROUND OF THE INVENTION

Laparoscopic surgery is one type of minimally invasive surgery in which a surgeon uses numerous trocar ports to access a tissue site of interest within the abdominal cavity of a patient. The benefits of laparoscopic surgery, as compared to open incisional, abdominal surgery, include less pain, shorter recovery time, less scarring, and lower cost. Endoscopic surgery affords another way to access the abdominal cavity via natural openings (mouth, anus, vagina, urethra) of the body and through the peritoneal lining of the abdominal cavity. Obviously, the size and shape of instruments that may be passed through a body lumen in order to perform a medical procedure in the abdominal cavity are greatly restricted due to the anatomical properties of the lumen.

General surgeons, gastroenterologists, and other medical specialists routinely use flexible endoscopes for intralumenal examination and treatment of the upper gastrointestinal (GI) tract, via the mouth, and the lower GI tract, via the anus. In these procedures, the physician advances the flexible endoscope through the lumen, periodically pausing to articulate the distal end of the endoscope using external control knobs, to redirect the distal tip of the endoscope. In this way, the physician may navigate the tortuous passageway of the upper GI past the pharynx, through the esophagus and gastro esophageal junction, and into the stomach. The physician must take great care not to injure the delicate mucosal lining of the lumen, which generally may stretch open to a diameter in the range of about 15-25 mm, but normally has a non-circular cross sectional configuration when relaxed.

During such translumenal procedures, a puncture must be formed in the stomach wall or in the gastrointestinal tract to access the peritoneal cavity. One device often used to form such a puncture is a needle knife which is inserted through the working channel of the endoscope, and which utilizes energy to penetrate through the tissue. A sphinctertome can then be inserted and reinserted into the tissue to expand the puncture made by the needle knife to form a multidirectional incision in the tissue. While effective, such a procedure for forming multidirectional incisions in tissue is time consuming and can also cause unnecessary distress to the tissue.

Accordingly, there remains a need for improved surgical cutting devices.

SUMMARY OF THE INVENTION

The present invention provides various devices and methods for forming a cut in tissue. In one aspect, a device for cutting tissue is provided that includes a flexible elongate member and a first tissue cutting wire that extends along the member. The first tissue cutting wire can have a first portion that is constrained with respect to the member, a distal portion that is anchored to the member, and an unconstrained portion that is adjacent to a first bend region on the member. The device can also include second and third tissue cutting wires that extend along the member and which have first portions that are constrained with respect to the member, distal portions that are anchored to the member, and unconstrained portions that are adjacent to second and third bend regions on the member, respectively. The unconstrained portions of the first, second, and third wires can be adapted to move from a delivery configuration to a cutting configuration to effect cutting of tissue upon the selective application of tension the wires.

The wires can have a variety of orientations with respect to the member to effect formation of a multidirectional cut. In one embodiment, the unconstrained portions of the first, second, and third wires can be circumferentially spaced from one another about the member, and can be positioned at the same longitudinal position on the member.

The first portions of the wires can be constrained, and the distal portions of the wires anchored, using a variety of techniques. In one embodiment, the wires can be constrained within and anchored to lumens or guide channels formed in the elongate member. In another embodiment, the wires can be constrained and anchored by a plurality of spaced retaining members positioned on the member. Additionally, the distal portions of the wires can be anchored to the member at a position that is offset from a longitudinal axis of the member to facilitate bending of the member.

The device can also include a variety of other features, such as a central working channel that extends between the proximal and distal ends of the member. The central working channel can have an incising element disposed therein and/or can be adapted to receive a guide device or an incising element.

In another aspect, a device for cutting tissue includes a flexible elongate member having proximal and distal ends, a first guide channel extending along a portion of the member, a second guide channel extending along a portion of the member and that is angularly spaced along a circumference of the member relative to the first guide channel, and a third guide channel that extends along at least a portion of the member and that is angularly spaced along a circumference of the member relative to the second guide channel. The first guide channel can include a first tissue-cutting wire that has a proximal end slidably disposed therein and an exposed portion that extends distally beyond the first guide channel. Similarly, the second and third guide channels can include second and third tissue-cutting wires having proximal ends slidably disposed therein and exposed portions that extend distally beyond the second and third guide channels, respectively. The device can also include an actuator coupled to the proximal ends of the first, second, and third wires. The actuator can be adapted to selectively apply tension to the first, second, and third wires that is effective to bend the member and expose a portion of the wire which extends distally beyond the guide channels to cause the device to assume a cutting configuration in which the wire is exposed relative to the member.

The exposed portions of the first, second, and third tissue-cutting wires can be positioned at a variety of locations along the member. In one embodiment, the exposed portions of the first, second, and third tissue-cutting wires can be circumferentially spaced about the member and optionally positioned at the same longitudinal position on the member.

The guide channels can have a variety of configurations, and in one embodiment the guide channels can be lumens that are formed in or along the flexible elongate member. In another embodiment, the guide channels can be formed from a plurality of spaced retaining members located on the elongate member. The device can also include a variety of other features to facilitate cutting tissue, such as at least one central working channel that extends between the proximal and distal ends of the member. The central working channel can be adapted to have an incising element movably disposed therein and/or to receive a guide device or incising element.

Methods for cutting tissue are also provided. In one aspect, a method for cutting tissue includes inserting a selectively bendable, elongate flexible cutting member into a lumen of a body. The member can have at least three tissue-cutting wires extending therealong, and the wires can be at least partially exposed with respect to the member. The method can further include selectively applying tension to at least one of the wires to cause the member to bend adjacent to the exposed portion of the wire thereby separating the wire from the member so that it assumes a tissue-cutting orientation. Energy can be delivered to the wire(s) when it is in the tissue-cutting orientation to effect cutting of a tissue.

For example, and in one embodiment, tension can be selectively applied to a first of the wires. This causes the member to bend in a first direction to separate a first tissue-cutting wire segment from the member such that the wire segment is in a position to form a cut in tissue. Thereafter tension can be selectively applied to a second of the wires to cause the member to bend in a second direction to separate a second tissue-cutting wire segment. In this position, the second wire segment can then form a second cut in the tissue, and the second cut can be formed in a different direction than the first cut. Tension can then be applied to a third of the wires to cause the member to bend in a third direction to expose a third tissue-cutting wire segment. A third cut can be formed in the tissue, and the third cut can be formed in a direction that is different than the direction of the first and second cuts. When the first tissue-cutting wire segment is positioned at an angle relative to the second tissue-cutting wire segment, and the second tissue-cutting wire segment is positioned at an angle relative to the third tissue-cutting wire segment, the method can further include rotating the member within the tissue to position the second and third tissue-cutting wire segments at the tissue to effect cutting.

The method can also include a variety of other steps to facilitate the formation of a cut in tissue, such as forming an incision in the tissue prior to the insertion of the member using an incising element disposed within a central working channel of the member or controlling an amount of tension applied to the wires such that the device can be positioned at a desired location in tissue. Additionally or alternatively, the method can include using a guidewire to position the member within the tissue.

BRIEF DESCRIPTION OF THE DRAWINGS

The invention will be more fully understood from the following cetailed description taken in conjunction with the accompanying drawings, in which.

DETAILED DESCRIPTION OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

The present invention provides devices and methods that can be used to form multidirectional cuts in tissue, such as tridirectional cuts. The tissue cutting devices disclosed herein generally include a flexible elongate member with at least first, second, and third wires that are at least partially constrained within or along a portion of the member. A distal portion of the wires is anchored on or within a portion of the elongate member. When tension is applied to at least one of the wires, such as by an actuator at a proximal end of the device, the elongate member bows while an unconstrained portion of the wire(s) becomes spaced from and exposed relative to the adjacent portion of the elongate member, assuming a tissue-cutting configuration.

Such a device is useful, for example, in transgastric surgical procedures where it is necessary to form incisions in tough stomach tissue. After puncturing the tissue, for example using a needle knife that can be integrated with or separate from the elongate member, the elongate member is advanced through the puncture to a desired position. The elongate member can then be oriented in the cutting configuration, and energy can be applied to the exposed wire to form a cut in tissue. The device can then be manipulated within the tissue (e.g., rotated) and tension can be applied to another wire. This causes the elongate member to bend in a different direction and expose a different wire in a different cutting configuration that is effective to cut tissue in a different direction. A second cut can then be formed in the tissue in a direction that is different from the first cut. The device can then again be manipulated in the tissue and tension can be applied to the third wire to form a third cut in the tissue, which extends in yet another direction. One skilled in the art will appreciate that while the tissue cutting devices disclosed herein are described primarily in the context of transgastric surgeries, they are applicable to a variety of surgical procedures, including intestinal surgeries to remove polyps and/or cancer treatment procedures.

FIGS. 1A-1D illustrate one embodiment of a device 110 for forming a tridirectional cut in tissue. As shown, the device 110 includes a flexible elongate member 112 having proximal and distal ends 112a, 112b and first, second, and third guide channels 130, 132, 134 that extend along at least a portion of the member 112 and house first, second, and third tissue-cutting wires 122, 123, 124. The wires 122, 123, 124 each have first portions that can be constrained within the guide channels 130, 132, 134 and distal portions that can be anchored within the guide channels 130, 132, 134. Each wire 122, 123, 124 also has an unconstrained portion that extends outside of the guide channels 130, 132, 134. The unconstrained portion of the wires 122, 124, 134 can be recessed within grooves 136, 137, 138 formed on the member 112 when the device 110 is in the delivery configuration. In use, tension can selectively and individually be applied to the wires 122, 123, 124 to cause the wires 122, 123, 124 to sequentially or simultaneously move from the delivery configuration to the tissue-cutting configuration to effect the cutting of tissue. Once the wires 122, 123, 124 are in the cutting configuration, energy can be selectively and individually applied thereto to effect the sequential or simultaneous cutting of tissue.

Figure 1A:
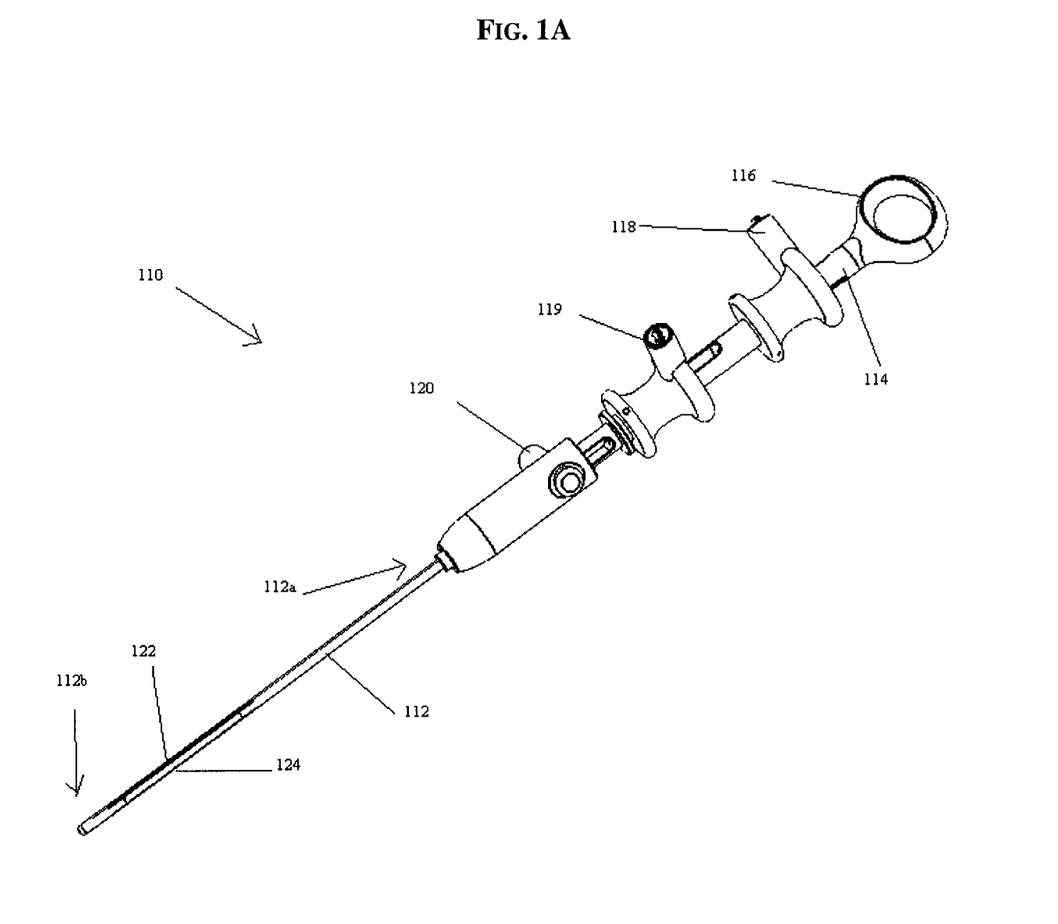
FIG. 1A is a perspective view of one embodiment of a surgical cutting device in a delivery configuration.
Figure 2A:
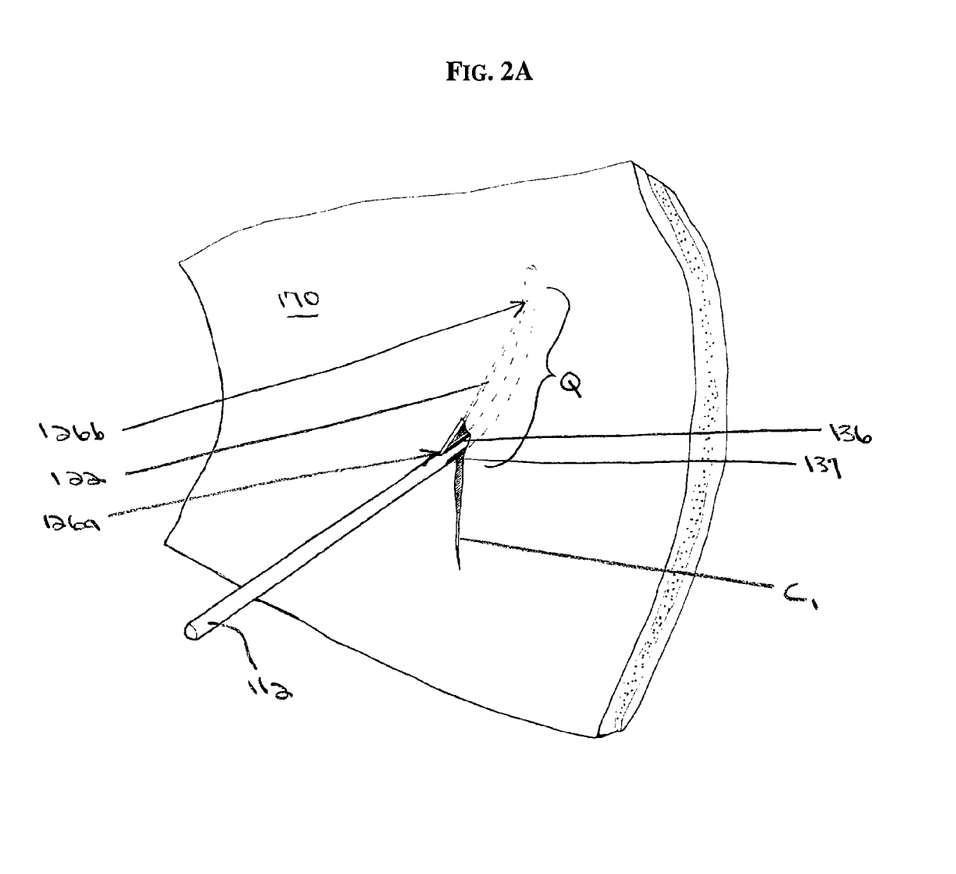
FIG. 2A is a schematic illustrating the device of FIG. 1A forming a first cut in tissue.
Figure 2B:
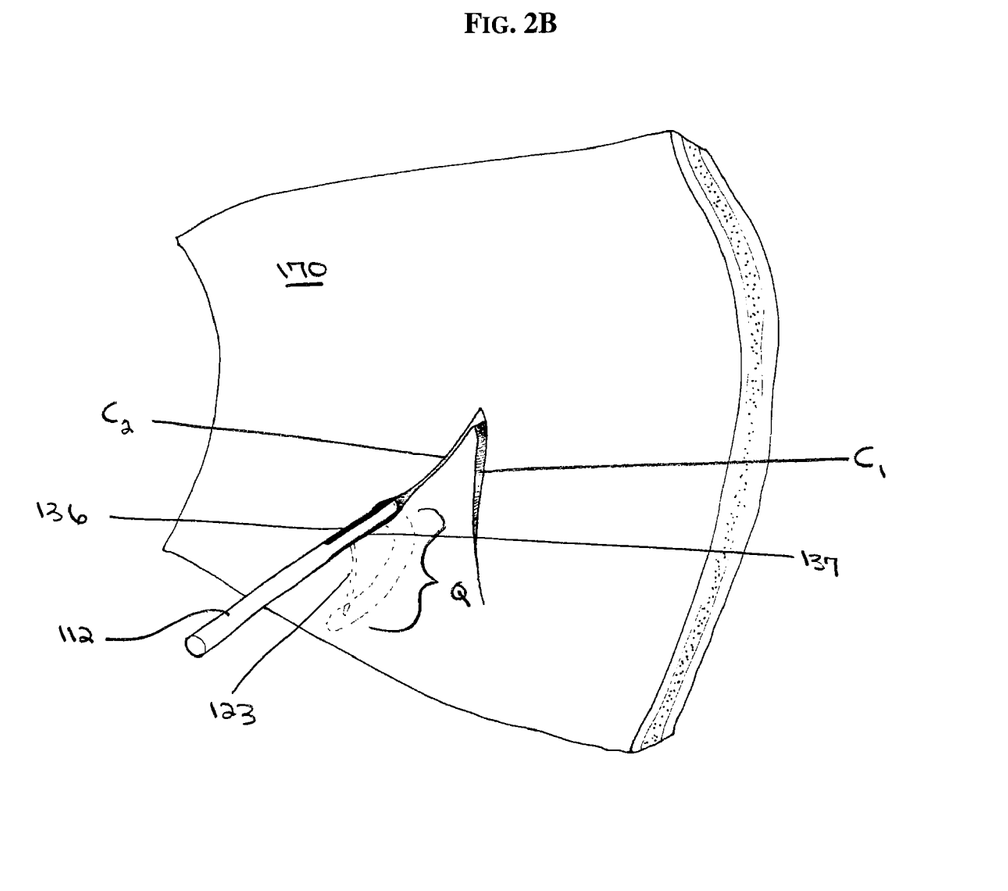
FIG. 2B is a schematic illustrating the device of FIG. 1A forming a second cut in tissue.
Figure 2C:
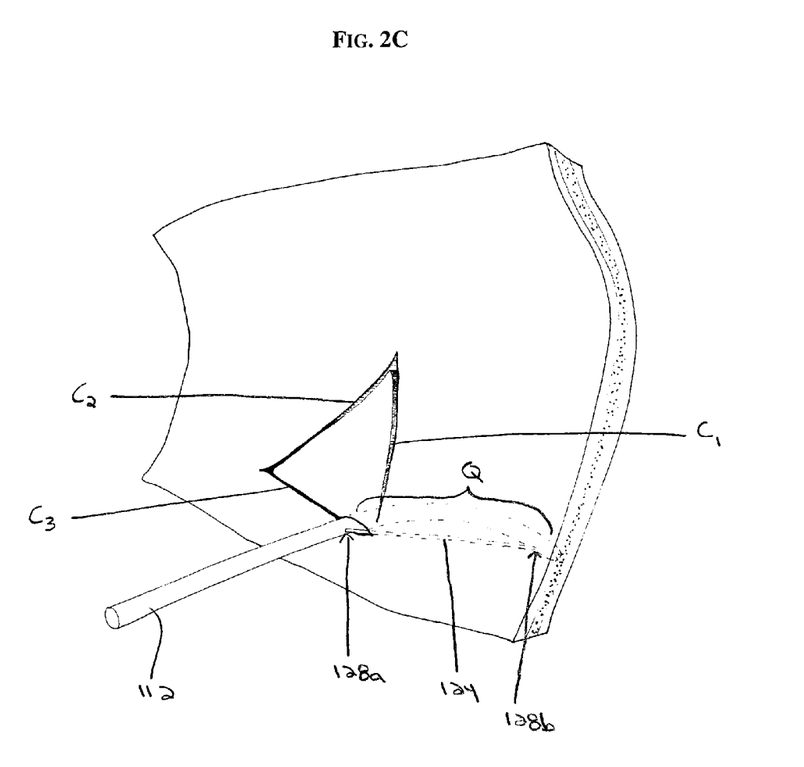
FIG. 2C is a schematic illustrating the device of FIG. 1A forming a third cut in tissue.

FIG. 1A illustrates the device 110 in the delivery configuration, in which the member 112 has a relatively straight or linear configuration and the unconstrained portions of the wires 122, 123, 124 are located adjacent to and in close proximity to the member 112. The unconstrained portions of the wires 122, 123, 124 can also rest within the grooves 136, 137, 138 that form recesses on the member 112 to facilitate ease of delivery to the target site in the tissue. Following the placement of the device 110 within tissue, the wires 122, 123, 124 can be selectively and individually tensioned to move from the delivery configuration to the tissue cutting configuration. As tension is applied, the member 112 in the bend region Q, adjacent to the wires, is caused to bend or bow such that the wire 122 separates from the member 112. Although FIG. 2C illustrates only one wire (122) under tension to cause the adjacent section of the member 112 to bend toward it, it is understood that each of the wires 123, 124 can be selectively and independently tensioned to effect bending of the member 112 in other directions, as shown in FIGS. 2A-2C and as will be discussed in more detail below.

Figure 1B:
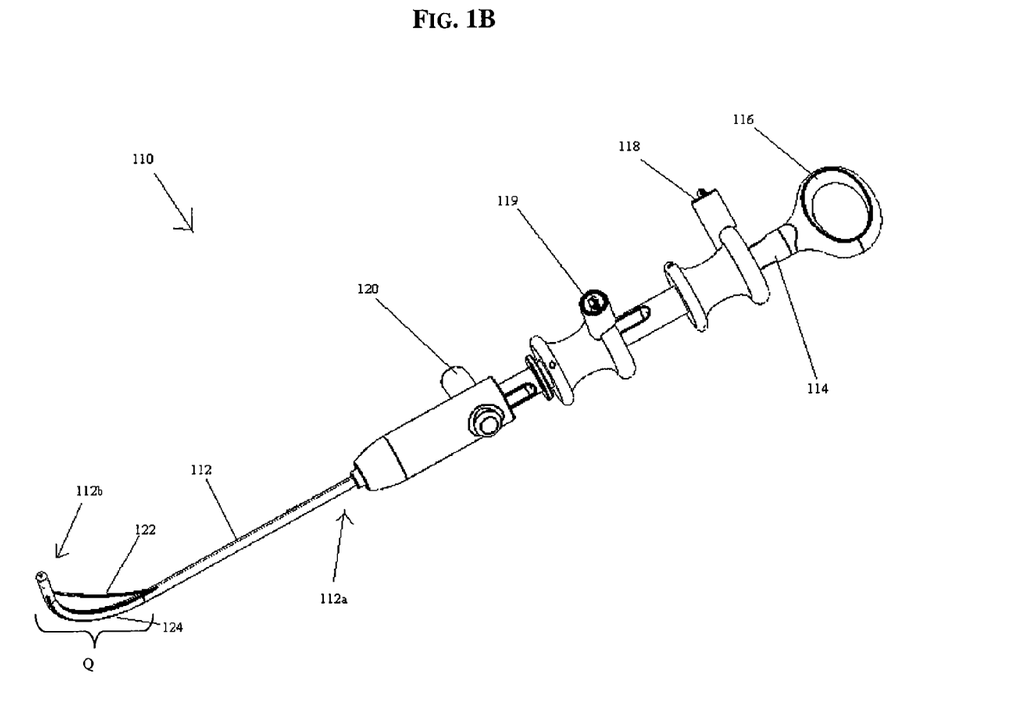
FIG. 1B is a perspective view of the device of FIG. 1A in a cutting configuration.
Figure 1C:
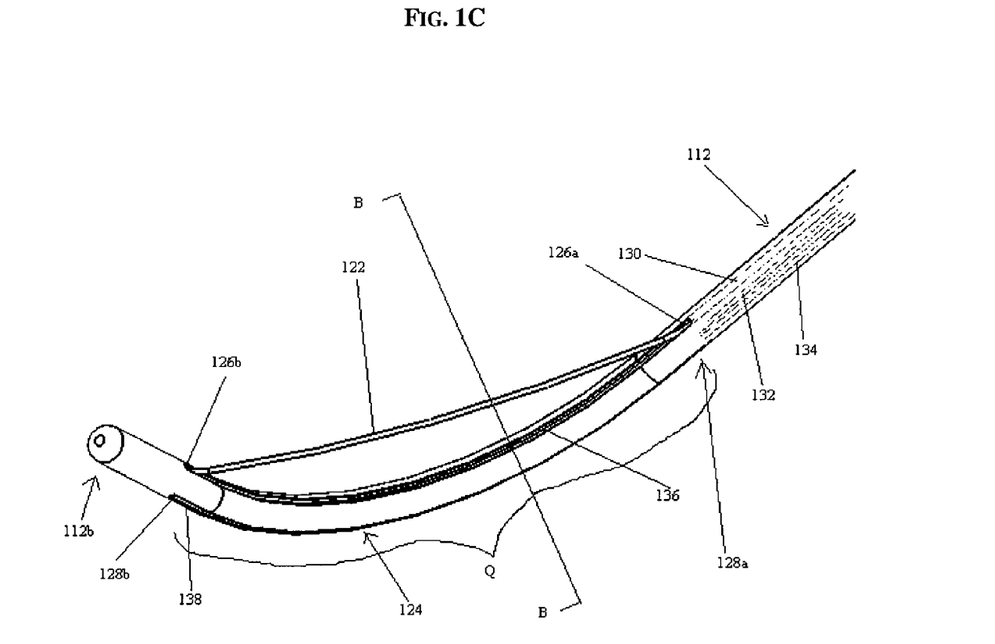
FIG. 1C is a perspective view of a distal end of a member of the device of FIG. 1B.
Figure 1D:
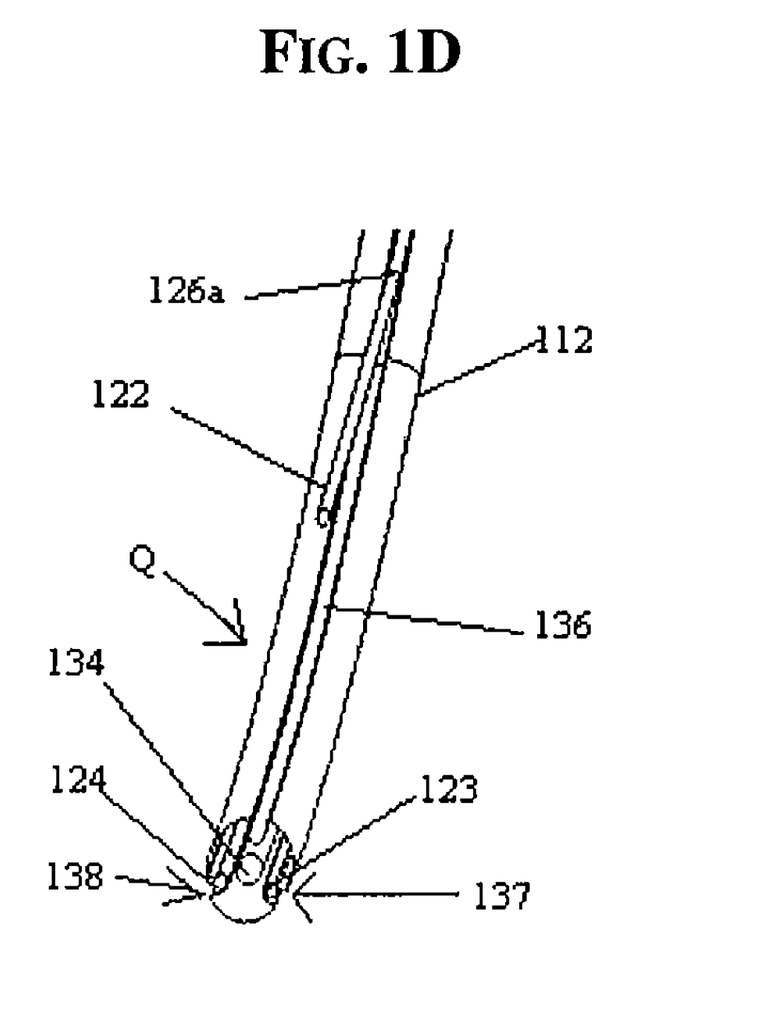
FIG. 1D is cross-sectional view of a mid-portion of the member of the device of FIG. 1B taken across line B-B.

The flexible elongate member 112 can have virtually any configuration that allows it to be laparoscopically or endoscopically inserted to a surgical site. As shown, the member 112 is substantially cylindrical and sufficiently strong to be inserted into tissue, yet flexible enough to bend upon the application of tension to the wires 122, 123, 124. The member 112 can include openings (openings 126a, 126b, 128a, 128b are shown in FIG. 1C) that correspond to openings in the guide channels 130, 132 to allow a portion of the wires 122, 123 to exit and reenter the guide channels 130, 132 and the member 112, such that they are unconstrained from the guide channels 130, 132. The member 112 can also include a groove or other receiver (groove 136, 137, 138 is shown in FIG. 1D) that is formed in the outer surface of the member 112 between the openings 126a, 126b, 128a, 128b. The grooves can be adapted to hold the unconstrained portions of the wires 122, 123, 124 adjacent to the member 112 in a recessed condition when the device 110, or at least a portion thereof, is in a delivery configuration. This is particularly advantageous in that it protects the wires 122, 123, 124 and tissue from damage during insertion of the device 110. The distal end 112b of the elongate member 112 can be adapted to facilitate insertion into tissue, and as shown in FIGS. 1A-1C, the distal end 112b can be tapered and/or rounded. Alternatively or additionally, the distal end 112b of the member 112 can include markings (not shown) formed thereon to facilitate positioning of the device 110 within tissue. While the member 112 can have a variety of sizes, and the size of the member 12 can depend upon the application of the device 110 and the type of tissue to be cut, in an exemplary embodiment, the member 112 can have a diameter in the range of about 2.0 mm to 3.5 mm, and more preferably about 2.4 mm.

One skilled in the art will appreciate that the device 110 can also include a variety of features to facilitate the formation of a cut in the tissue. As shown in FIG. 1D, the member 112 can include at least one working channel 134 that can be centrally positioned and that extends therethrough. The working channel 134 can be adapted to hold a guide device, such as a guidewire, to facilitate positioning of the device 110 within tissue. Optionally or additionally, the working channel 134 can house an incising element (not shown) for forming an initial incision within the tissue. One skilled in the art will appreciate that the incising element can have a variety of configurations and can be integrated within the working channel or it can be a separate device that is inserted within the working channel. One exemplary incising element that can be used with the devices disclosed herein is the incising element employed in the integrated guidewire needle knife that is disclosed in commonly owned application entitled "Integrated Guidewire Needle Knife," filed concurrently herewith, the disclosure of which is incorporated by reference herein.

Referring back to FIGS. 1A-1B, a handle 114 can be located on the proximal end 112a of the member 112 to facilitate manipulation and handling of the device 110. The handle 114 can have any configuration that allows a user to conveniently hold and operate the device 110. In one embodiment however, the handle 114 has a substantially elongate shape and includes a thumb ring 116 to facilitate grasping. The handle 114 can also include at least one actuator that enables tension to be selectively applied to the tissue-cutting wires 122, 123, 124. In one embodiment, the handle 114 also includes first, second, and third sliding actuator levers 118, 119, 120 that are coupled to the first, second, and third wires 122, 123, 124, respectively. In alternate embodiments, rotatable knobs or dials can be used to selectively apply tension to the wires. A locking mechanism (not shown) can also be associated with the tension applying mechanism to hold the wires 122, 123, 124 in position once tension is applied. In use, the levers 118, 119, 120 can be moved in the proximal direction to apply tension to the wires 122, 123, 124, causing the wires 122, 123, 124 and the member 112 move from a delivery configuration to a tissue-cutting configuration. Once in the tissue-cutting configuration, the wires 122, 123, 124 can be locked in position using the locking mechanism.

While a variety of locking mechanisms can be used, one exemplary locking mechanism can include a clamp that is effective to clamp down onto the wires and thereby prevent movement of the wires such that the device is held in the desired orientation. The clamp can have a variety of shapes and sizes, and it can be positioned at various locations on the device. In one embodiment, the clamp can be disposed within the handle. In an initial position, the clamp is spaced apart from the wires to allow free movement thereof. Once the wires are tensioned and the bend regions bent, the clamp can be moved until it engage the wires within the handle. The clamp will thus prevent movement of the wires when the clamp is in the locked position. In order to lock the clamp, the clamp can include a mating element formed thereon and configured to engage a corresponding mating element formed in the handle. For example, the clamp can include threads formed therein that are configured to mate with corresponding threads in the handle. As a result, rotation of the clamp about the handle will cause the clamp to move between the initial and locked positions. While the exemplary mating technique includes threads, one skilled in the art will appreciate that various other mating techniques can be used.

The handle 114 can also optionally be adapted to facilitate the delivery of energy to the wires 122, 123, 124 to cut tissue. An energy source (not shown), such as a battery that is in electrical communication with the wires, can be disposed within the handle. Alternatively, the handle can be adapted to be coupled to an external energy source, such as a generator or an outlet. The handle can also include a mechanism that facilitates the selective delivery of energy to the wires, such as a button or knob that can cause activation of the energy source. While the exemplary embodiment illustrates an elongate handle 114, one skilled in the art will appreciate that the handle can have any configuration that allows a user to selectively apply tension as well as energy to the wires, such as a joystick control.

As noted above, first, second, and third guide channels 130, 132, 134 extend along at least a portion of the member 112 for constraining portions of the wires 122, 123, 124 relative to the member 112. The guide channels 130, 132, 134 can extend along the member 112 in a variety of orientations to help effect multidirectional bending of the device, however as shown, the guide channels 130, 132, 134 are circumferentially spaced about the member 112 (e.g., radially disposed about the circumference of the member 112). The circumferential spacing of the guide channels 130, 132, 134 and hence the wires 122, 123, 124 enables the tridirectional bending of the member 112. The exposed portions of each of the wires 122, 123, 124 can be at the same longitudinal level of the member 112, as shown in FIGS. 2A-2C, or they can be at different longitudinal levels. As a result, the member 112 has a bend zone Q. This configuration, as will be described below, enables the device 110 to be inserted into tissue, and then configured into a cutting configuration to form a cut in one direction using wire 122. The member 112 can then be configured in a cutting configuration to cut tissue in another direction with wire 123, and a third direction with wire 124, such that a tridirectional cut is formed in the tissue.

The circumferential spacing of the guide channels 130, 132, 134 and hence the wires 122, 123, 124, also influences the shape of the resulting cut. While the guide channels 130, 132, 134 can be separated by virtually any range of angles, in one embodiment the guide channels 130, 132, 134 are equally spaced (i.e., by about 120°) about the member 112. This configuration can result in the formation of a substantially triangular cut in tissue.

In particular, FIG. 2C illustrates one embodiment in which at least a proximal portion of the guide channel 130 is disposed within a proximal portion of the member 112. The guide channel 130 can extend through the proximal portion of the member 112 to an opening 126a, which marks the termination of a proximal portion of the guide channel 130. A wire, such as wire 122 shown in FIG. 2C, can extend through the guide channel 130, which maintains it in a constrained position, emerge through the opening 126a, and extend along the member 112 in an external, unconstrained position until it is anchored back within another opening 126b. The opening 126b can form the entry to a distal portion of the guide channel 130, or it can simply form a termination point for the wire 122.

Guide channels 132 and 134 are circumferentially spaced and angularly offset from guide channel 130 and are similarly constructed. That is, guide channels 132 and 134 each have a proximal portion that constrains a wire and an opening (opening 128a is shown in FIG. 2C) through which the wire emerges to an external, unconstrained position. Each of guide channels 132, 134 can also have an opening (opening 128b is shown in FIG. 2C) analogous to opening 126b within which a distal portion of the wire can be anchored. While the exemplary embodiment illustrates guide channels 130, 132, 134 that are positioned at the same longitudinal position on the member 112, in other embodiments the guide channels can be longitudinally separated and radially offset from one another by a range of degrees, such as, for example, about 90° or about 180°, depending upon the type of cut desired.

The guide channels 130, 132, 134 can have a variety of configurations, however as shown in FIG. 1D, the first and second guide channels 130, 132, 134 are lumens. In other embodiments, however, the guide channels can be retaining members, such as guides, clips, or fasteners, that are located on the outside of the member. The retaining members can be relatively closely spaced to hold the wires in a constrained position and more widely spaced to form the unconstrained portion of the wires.

As noted above, a distal portion of each of the wires 122, 123, 124 is anchored to the member 112, for example, within a distal portion of its respective guide channel 130, 132, 134. A variety of techniques can be used to anchor the distal portions of the wires 122, 123, 124, such as welding, knots, adhesives, or other fasteners. In one embodiment, the inside of the guide channels can include hooks or some other fastener, and the distal end of the wires can be attached to such hooks or fasteners. The distal ends of the wires 122, 123, 124 can also be anchored within the guide channels 130, 132, 134 at a position that is offset from the longitudinal axis of the member 112. As a result, and upon the application of tension to the wires 122, 123, 124 the wires 122, 123, 124 can act as a lever arm to facilitate bending of the member 112. The proximal ends of each of the wires 122, 123, 124 can be disposed within the guide channels 130, 132, 134 and coupled to a tension applying mechanism, such as the actuation levers 118, 119, 120 located on the handle 114 as described above. A proximal portion of the wires 122, 123, 124 can also be in electrical communication with, for example, a source of RF energy.

The wires 122, 123, 124 can be formed from a variety of materials that are suitable to cut tissue. In one embodiment, the wires 122, 123, 124 are made from a conductive material such that the tissue can be cut via electrosurgical energy. Exemplary materials can include stainless steel, nitinol, carbon steel, aluminum, and combinations thereof. One skilled in the art will appreciate that the wires can also have a variety of sizes depending upon the type of tissue to be cut. In one embodiment, however, the wires can have a diameter in the range of about 0.005 inch to 0.025 inch, and more preferably about 0.015 inch.

While the exemplary embodiment illustrates a device 110 having three wires 122, 123, 124, one skilled in the art will appreciate that the device can have any number of wires in any number of configurations to form a variety of multidirectional cuts in tissue.

The device disclosed herein can be used in surgical procedures in the manner described below. Following preparation of the patient as known in the art, the member can be inserted into a natural or created orifice to a target site. As noted above, the device 110 is typically inserted in the delivery configuration shown in FIG. 1A, where the member 112 has a substantially linear configuration and the wires 122, 123, 124 are located adjacent to the member 112 and optionally recessed within the grooves 136, 137, 138. A variety of techniques can be used to insert the device into the orifice, and in one embodiment a guide device, such as a guidewire, can be positioned within a central working channel of the device and used to guide the device to the target site. Once at the target site, the guide device can be removed from the working channel and optionally replaced by an incising element. Alternatively, in embodiments where the device includes an additional working channel for a treatment device, the incising element can be inserted in such a working channel while the guide device remains in place. In either embodiment, the cutting device can then be used to form an initial perforation in the tissue. A variety of incising elements can be used, however in one exemplary embodiment an integrated guidewire needle knife device can be used, such as that disclosed in commonly owned application entitled "Integrated Guidewire Needle Knife," filed concurrently herewith, the disclosure of which is incorporated by referenced herein.

Following the formation of the initial perforation, the device can be further advanced through the perforation so that an exposed portion of a wire to be used to cut tissue is properly positioned adjacent to the tissue to be cut. Thereafter, the member is moved to the cutting configuration. This can be effected by applying tension to one or more of the wires, which causes the portion of the member that is adjacent to the unconstrained portion of the wire to bend or bow, such that the unconstrained portion of the wire moves from a position adjacent to the member to a position spaced a distance away from the member and in a cutting configuration. For example, FIG. 2A illustrates the device 110 where tension is applied to wire 122 such that the bend region Q is bowed and the wire 122 is in the cutting configuration. In alternate embodiments, tension is simultaneously applied to the wires 122, 123, and/or 124 such that bend region Q is bowed and the wires 122, 123 and/or 124 are in the cutting configuration. Once the wire is positioned in the cutting configuration, the locking mechanism can optionally be activated to maintain the position of the wire(s).

At this point, energy, such as RF energy, can be delivered to the tensioned wire(s) by, for example, using an energy delivery mechanism on the handle. This causes the wire(s) to penetrate the tissue, forming a cut in the tissue. For example, FIG. 2A illustrates the device 110 being used to form a first cut $C_1$ in tissue 170 using wire 122. Following the formation of the cut $C_1$, the energy delivery can cease, and the locking member can optionally be released, causing the member to return to its delivery configuration. The device can then be slightly rotated within the tissue such that the second wire 123 is aligned with the direction of intended cutting, which is different than the direction of the first cut $C_1$. Tension can be applied to the second wire 123, if it is not tensioned already, to cause a portion of the device Q that is adjacent to the second wire 123 to bend while the second wire 123 extends a distance away from the member 112 to assume a tissue cutting configuration. Energy can then be delivered to the second wire 123 to form a second cut $C_2$, as shown in FIG. 2B. Following formation of the second cut $C_2$, the application of energy to the wire 123 can cease, and the tension can optionally be released, causing the member 112 to return to its delivery configuration. The device can then be rotated again such that the third wire 124 is aligned with the intended direction of the third cut, which will be different than the direction at least of the first and second cuts $C_1$, $C_2$. Tension can then be applied to the third wire 124, if the third wire is not already tensioned, such that it assumes a tissue-cutting configuration, and energy can be delivered to the third wire 124 to cause a third cut $C_3$ to be formed in tissue, as shown in FIG. 2C. The resulting shape from the first, second, and third cuts $C_1$, $C_2$, $C_3$ is substantially triangular.

Although the above methods use the sequential tensioning of the wires 122, 123, 124 to form a multidirectional cut in tissue, one skilled in the art will appreciate that the wires can also be simultaneously tensioned and energy applied to one, two or all of the tensioned wires to form a cut in tissue. The simultaneous tensioning of the wires is particularly advantageous in that it can facilitate positioning the device in tissue. For example, and referring back to FIG. 2B, as energy is applied to the wire 122, tension can be selectively applied to the wire 123. This results in the device bending at a location that is approximately midway between the planes of wire 122 and wire 123. Additionally, and upon the application of energy to two or more of the tensioned-wires, the device can be used to form a large incision in tissue, such as to cut a large otomy in an organ in order to gain access to the adjacent space.

Cutting devices, including components thereof, can be designed to be disposed after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. By way of example, the devices disclosed herein can be reconditioned after the device has been used in a medical procedure. The device can be disassembled, and any number of the particular pieces (e.g., the wires, the member, or the handle) can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a cutting device can utilize a variety of techniques for disassembly, cleaning/replacement, and reassembly. Use of such techniques, and the resulting reconditioned cutting device, are all within the scope of the present application.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A device for cutting tissue, comprising:
a flexible elongate member;
a first tissue cutting wire extending along the member having a first constrained portion with respect to the member, a distal portion anchored to the member, and an unconstrained portion that is adjacent to a first bend region on the member;
a second tissue cutting wire extending along the member having a first constrained portion with respect to the member, a distal portion anchored to the member, and an unconstrained portion that is adjacent to a second bend region on the member; and
a third tissue cutting wire extending along the member having a first constrained portion with respect to the member, a distal portion anchored to the member, and an unconstrained portion that is adjacent to a third bend region on the member,
wherein the unconstrained portions of the first, second, and third wires are adapted to be selectively tensioned to move from a delivery configuration to a cutting configuration to effect cutting of tissue.

2. The device of claim 1, wherein the unconstrained portions of the first, second, and third wires are circumferentially spaced from one another about the member.

3. The device of claim 1, wherein the unconstrained portions of the first, second, and third wires are positioned at a same longitudinal position on the member.

4. The device of claim 1, wherein the wires are conductive.

5. The device of claim 1, wherein the first, second, and third wires are constrained by and anchored to first, second, and third lumens formed within the member.

6. The device of claim 1, wherein the first, second, and third wires are constrained by and anchored by a plurality of spaced retaining members positioned on the member.

7. The device of claim 1, wherein the distal portions of the first, second, and third wires are anchored at a position that is offset from a longitudinal axis of the member.

8. The device of claim 1, further comprising at least one central working channel extending between proximal and distal ends of the member.

9. A device for cutting tissue, comprising:
- a flexible elongate member having proximal and distal ends;
- a first guide channel extending along at least a portion of the member, the first guide channel having a proximal portion and a distal portion;
- a first tissue-cutting wire having a proximal end disposed within the proximal portion of the first guide channel, and an exposed portion extending between and outside of the proximal and distal portions of the first guide channel;
- a second guide channel extending along at least a portion of the member such that it is angularly spaced along a circumference of the flexible elongate member from the first guide channel, the second guide channel having a proximal portion and a distal portion;
- a second tissue-cutting wire having a proximal end disposed within the proximal portion of the second guide channel, and an exposed portion extending between and outside of the proximal and distal portions of the second guide channel;
- a third guide channel extending along at least a portion of the member such that it is angularly spaced along a circumference of the flexible elongate member from the second guide channel, the third guide channel having a proximal portion and a distal portion;
- a third tissue-cutting wire having a proximal end disposed within the proximal portion of the third guide channel and an exposed portion extending between and outside of the proximal and distal portions of the third guide channel; and
- an actuator coupled to the proximal ends of the first, second, and third wires and adapted to selectively and individually apply tension to the first, second, and third wires effective to bend the member to expose the wire to which tension is applied in a cutting configuration at the exposed portion of the wire.

10. The device of claim 9, wherein the exposed portions of the first, second, and third tissue-cutting wires are radially disposed around the circumference of the member.

11. The device of claim 9, wherein the exposed portions of the first, second, and third tissue-cutting wires are positioned at a same longitudinal position on the flexible elongate member.

12. The device of claim 9, wherein the first, second, and third tissue-cutting wires are conductive.

13. The device of claim 9, wherein the first, second, and third guide channels are lumens that are formed in the flexible elongate member.

14. The device of claim 9, wherein each guide channel is formed by a plurality of spaced retaining members.

15. The device of claim 9, further comprising at least one central working channel that extends between the proximal and distal ends of the member.

16. A method for cutting tissue, comprising:
- inserting a selectively bendable, elongate flexible cutting member into a lumen of a body, the member having at least three tissue-cutting wires extending therealong, the wires being at least partially exposed from the member;
- selectively applying tension to at least one of the wires to cause the member to bend adjacent to the exposed portion of the wire to configure the wire in a tissue-cutting orientation; and
- applying energy to the wire in the tissue-cutting orientation to effect cutting of a tissue.

17. The method of claim 16, further comprising:
- selectively applying tension to a first of the wires to cause the member to bend in a first direction exposing a first tissue-cutting wire segment and thereby forming a first cut in the first direction with the first tissue-cutting wire segment;
- selectively applying tension to a second of the wires to cause the member to bend in a second direction exposing a second tissue-cutting wire segment, the second direction being different than the first direction;
- forming a second cut in the second direction with the second tissue-cutting wire segment;
- selectively applying tension to a third of the wires to cause the member to bend in a third direction exposing the third tissue-cutting wire segment, the third direction being different than the first and second directions; and
- forming a third cut in the third direction with the third tissue-cutting wire segment.

18. The method of claim 17, wherein the first tissue-cutting wire segment is positioned at an angle relative to the second tissue-cutting wire segment, and the second tissue-cutting wire segment is positioned at an angle relative to the third tissue-cutting wire segment, and further comprising rotating the member within the tissue to position the second and third tissue-cutting wire segments at the tissue to effect cutting.

19. The method of claim 16, further comprising controlling an amount of tension applied to the wires such that the member can be positioned at a desired location in tissue.

20. The method of claim 16, further comprising forming an incision in the tissue prior to the insertion of the member therein using a incising element disposed within a working channel of the member.

21. The method of claim 16, further comprising using a guide device to position the member within the tissue.

* * * * *